(12) United States Patent
Hen et al.

(10) Patent No.: US 8,979,726 B2
(45) Date of Patent: Mar. 17, 2015

(54) HEMOSTASIS COMPOSITION WITH MAGNETITE

(71) Applicant: Biolife, L.L.C., Sarasota, FL (US)

(72) Inventors: John Hen, Bradenton, FL (US); Talmadge Kelly Keene, Wimauma, FL (US); Mark Travi, Venice, FL (US)

(73) Assignee: Biolife, L.L.C., Sarasota, FL (US)

( * ) Notice: Subject to any disclaimer, the term of this patent is extended or adjusted under 35 U.S.C. 154(b) by 0 days.

(21) Appl. No.: 13/760,319

(22) Filed: Feb. 6, 2013

(65) Prior Publication Data

US 2013/0150652 A1 Jun. 13, 2013

Related U.S. Application Data

(63) Continuation of application No. 12/719,434, filed on Mar. 8, 2010, now abandoned.

(60) Provisional application No. 61/209,359, filed on Mar. 6, 2009.

(51) Int. Cl.

| | |
|---|---|
| *A61K 33/26* | (2006.01) |
| *A61N 2/00* | (2006.01) |
| *A61K 9/00* | (2006.01) |
| *A61K 31/74* | (2006.01) |
| *A61L 15/42* | (2006.01) |

(52) U.S. Cl.
CPC ............... *A61K 33/26* (2013.01); *A61K 9/0009* (2013.01); *A61K 9/0014* (2013.01); *A61K 31/74* (2013.01); *A61L 15/42* (2013.01); *A61L 2400/04* (2013.01); *A61N 2/002* (2013.01)
USPC .............................. 600/9; 424/647; 424/78.06

(58) Field of Classification Search
CPC ... A61K 9/0014; A61N 2/002; A61L 2400/04
See application file for complete search history.

(56) References Cited

U.S. PATENT DOCUMENTS

| | | |
|---|---|---|
| 4,046,591 A | 9/1977 | Laguerre |
| 4,545,974 A | 10/1985 | Thompson |
| 4,551,326 A | 11/1985 | Thompson |
| 6,187,347 B1 | 2/2001 | Patterson et al. |
| 6,521,265 B1 | 2/2003 | Patterson |
| 6,790,429 B2 | 9/2004 | Ciampi |
| 6,946,078 B2 | 9/2005 | Minevski et al. |
| 6,974,562 B2 | 12/2005 | Ciampi et al. |
| 7,303,759 B2 | 12/2007 | Mershon |
| 7,476,324 B2 | 1/2009 | Ciampi et al. |
| 7,595,429 B2 | 9/2009 | Hursey |
| 2002/0197302 A1 | 12/2002 | Cochrum et al. |
| 2007/0269499 A1 | 11/2007 | Hen et al. |
| 2010/0151049 A1 | 6/2010 | Thompson et al. |

FOREIGN PATENT DOCUMENTS

| | | |
|---|---|---|
| CA | 2 369 921 A1 | 6/2003 |
| RU | 2125453 * | 1/1999 |
| WO | 2008151041 A2 | 12/2008 |

OTHER PUBLICATIONS

Moskowitz, Bruce M., Hitchhiker's Guide to Magnetism (2002). Accessed at http://irm.umn.edu/hg2m/hg2m.pdf on Aug. 29, 2011.

* cited by examiner

*Primary Examiner* — Jeffrey S Lundgren
*Assistant Examiner* — Sara E Townsley
(74) *Attorney, Agent, or Firm* — Charles J. Prescott

(57) ABSTRACT

A composition and method of arresting the flow of blood from a bleeding wound. The composition preferably includes an anhydrous salt ferrate compound preferably combined with an effective amount of an insoluble cation exchange material and an effective amount of anhydrous Magnetite mixed uniformly together. Povidone iodine may be added for enhanced antimicrobial properties. In the method, a quantity of the composition is magnetically attached to a surface of a magnet, after which the powderous mixture is applied to the wound by pressing the surface covered with the powderous compound against the wound for a time sufficient to clot the blood to arrest substantial further blood flow from the wound.

4 Claims, 4 Drawing Sheets

Figure 1. Pick Up as Functions of % Magnetite and Magnet Type
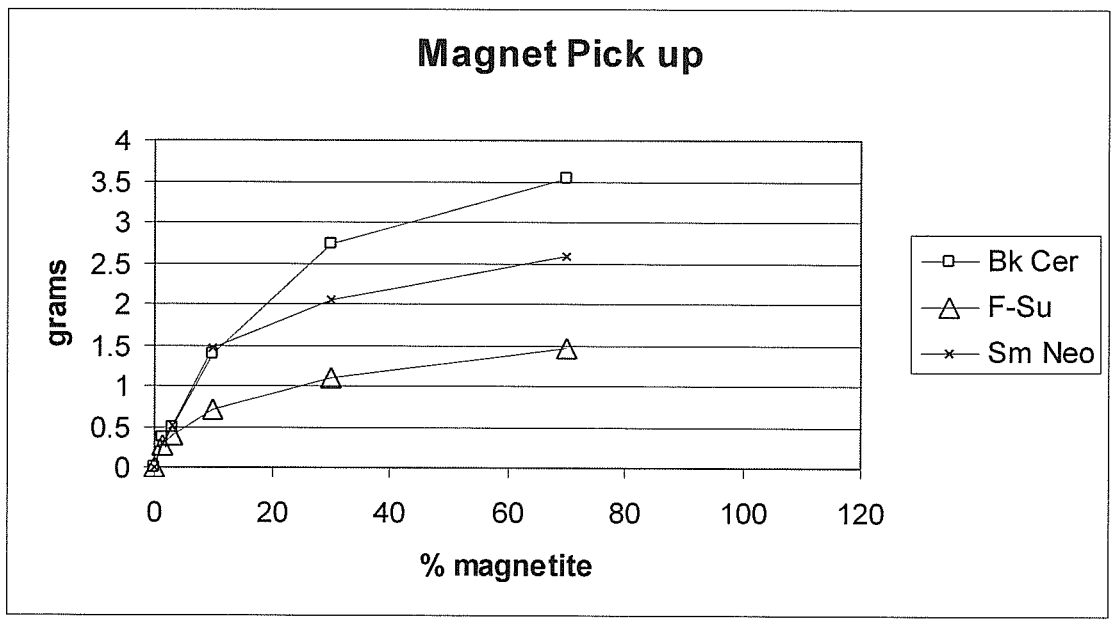
Figure 2. Pick Up of QR Containing 3% Magnetite
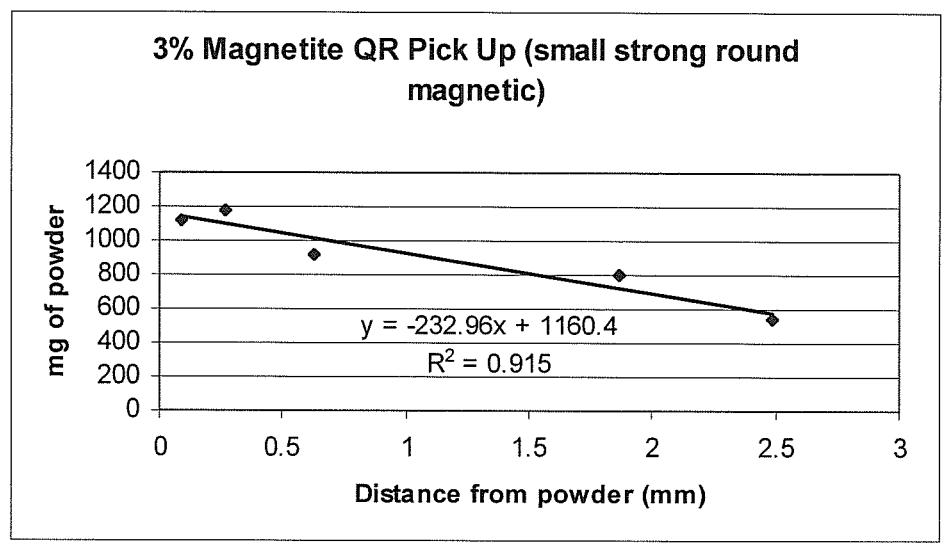

HEMOSTASIS COMPOSITION WITH MAGNETITE

CROSS-REFERENCE TO RELATED APPLICATIONS

This application is a continuation of application Ser. No. 12/719,434, filed Mar. 8, 2010, which is a nonprovisional of Application No. 61/209,359, filed Mar. 6, 2009.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This disclosure relates to improved delivery and control of hemostasis powder in vascular access procedures and in other hemostasis control procedures and more particularly to such compositions with Magnetite for enhanced control of the powdery composition.

2. Description of Related Art

Hemostasis powders are well known. Thompson et al, U.S. Pat. Nos. 4,545,974 & 4,551,326, disclose processes for the manufacture of potassium ferrate and similar high oxidation state oxyiron compounds. Patterson et al, U.S. Pat. No. 6,187,347 and Patterson et al, U.S. Pat. No. 6,521,265, disclose the mixing of potassium ferrate and anhydrous strongly acidic cation exchange resins for the cessation of bleeding. These patents are incorporated by reference herein in their entirety. Kuo et al. (J. Vasc Interv. Radiol. 19:1 72-79 2008) disclose the benefit of ferrate/resin mixtures in reducing the time to hemostasis (TTH) from 6 minutes to 4 minutes versus D-stat, the market leader in hemostasis pads. Michelson (The American Journal of Cosmetic Surgery 25-3 2008) shows that the ferrate/resin mixtures are excellent for wound care. Michelson demonstrated complete closure of a patient with twin brachial dehisced wounds following cosmetic surgery. After 16 weeks, the patient healed without scarring.

Thompson (U.S. Pat. No. 4,545,974 and U.S. Pat. No. 4,551,326) also teaches that Magnetite, $Fe_3O_4$, or iron oxide, $Fe_2O_3$ (common rust) are suitable substrates for making ferrate, $FeO_4^-$. But critically, the iron compounds have to be heated above the Curie point, that temperature at which a ferromagnetic material loses its ferromagnetic ability. For iron, the Curie point is 768° C. Thus Thompson teaches that potassium ferrate is not magnetic even if the starting raw material was magnetic.

The foregoing examples of the related art and limitations related therewith are intended to be illustrative and not exclusive. Other limitations of the related art will become apparent to those skilled in the art upon a reading of the specification and a study of the drawings.

BRIEF DESCRIPTION OF THE SEVERAL VIEWS OF THE DRAWING(S)

FIG. 1 depicts the relationship between percentage of Magnetite and the weight of powder picked up by selected magnets.

FIG. 2 depicts the amount of powder picked up by the magnet versus distance of the magnet from the powder.

Figure 3:
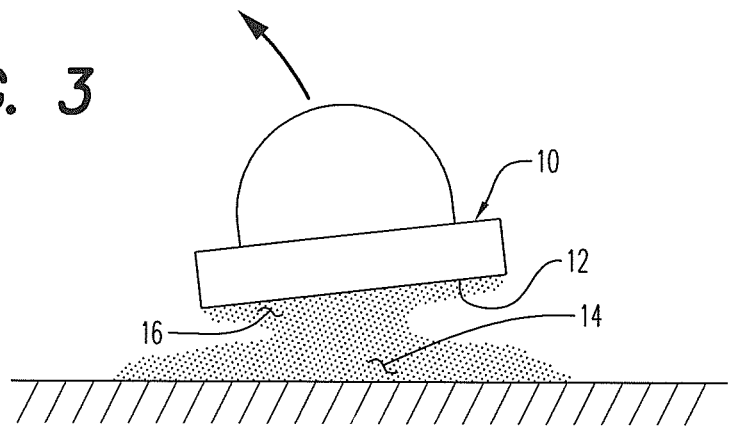
FIG. 3 is a simplified side elevation view of a magnetic picking up a quantity of hemostatic powder containing Magnetite.

Exemplary embodiments are illustrated in reference figures of the drawings. It is intended that the embodiments and figures disclosed herein are to be considered to be illustrative rather than limiting.

BRIEF SUMMARY OF THE INVENTION

This invention is directed to a composition and method of arresting the flow of blood from a bleeding wound. The composition preferably includes an anhydrous salt ferrate compound preferably combined with an effective amount of an insoluble cation exchange material (sometimes referred to as the "powder" or "powderous mixture") and an effective amount of anhydrous Magnetite mixed uniformly together. In the method, a quantity of the composition is magnetically attached to a surface of a magnet, after which the composition is applied to the wound by pressing the surface covered with the composition against the wound for a time sufficient to clot the blood to arrest substantial further blood flow from the wound.

Magnetite addition to a potassium ferrate/strong acid cation exchange resin powderous mixture provides greatly improved delivery and control of the application of the hemostasis powder onto the wound site. Adding Magnetite to a potassium ferrate/strong acid cation exchange resin mixture at room temperature did not decrease the strength of a blood seal. Correspondingly, adding Hematite reduced the strength of the blood seal.

Mechanism of Action

1. The preferred 1:7 ferrate: hydrogen resin mixed powder, as an adjunct to pressure, creates a nothing-in/nothing-out seal in well-known ways with blood.
    a. The external semi- or non-occlusive vertical pressure is critical to achieving hemostasis. Without pressure, hemostasis is not consistently achieved.
2. The powder is ground as part of the manufacturing process.
3. The Magnetite is preferably very fine, ~10 microns, but other sizes can be used.
4. The Magnetite is distributed throughout the powder, allowing a much greater mass of powder to be held than the amount of Magnetite in the mixture.

Magnetite is also a well-known colorant, for example often used in mascara. When Magnetite is added to the 1:7 powder, the mixture is gray-black, not brown color. The color difference distinguishes Magnetite powders from non Magnetite powder.

When powder mixtures are used for hemostasis, the bleeding surface is often not flat. Bone-dry powders tend to fall off the site at which they are aimed. Previously disclosed powder containment devices (PCD) are used to reduce the spillage.

They are not, however, completely reliable, particularly for stopping bleeding around catheter lines on vertical or near vertical surfaces as the powder pile can spill over the edge of the PCD. Mixing Magnetite with the powder will allow it to be applied, transported, or held in place with a magnet. The incorporation of Magnetite to the hemostatic powder allows dramatic improvements in the delivery and control during application on a wound site.

DETAILED DESCRIPTION OF THE INVENTION

Ferrate/resin mixtures at the preferred 1:7 (w/w) ratio are able to exchange H+ for dissolved cations, thus reducing pH. A typical cation exposure might be in a microbe attempting to penetrate a wound surrounding a catheter line. The microbe cell wall has mono- and divalent-cations for strength and life support plus ~85% moisture. The dry ferrate/resin mixture absorbs the cation-rich water and exchanges the cations for protons. The surface pH drops to ~2, creating a hostile environment for microbes.

In experiments, the 1:7 ferrate/resin mixture produced a >5 log kill on MRSA (Methicillin Resistant *Staphylococcus Aureus*, MRSE (Methicillin Resistant *Staphylococcus Epidermidis*), and VRE (Vancomycin Resistant Entorococci), a >4 log kill on *Candida* albicans, and no kill on *Aspergillus niger*. The experiments included a 7-day test with daily rechallenge.

Povidone Iodine

There are two active antimicrobial compounds approved as active OTC antimicrobials, i.e., >62% alcohol, and 5-10% povidone iodine (PI). Alcohol decomposes ferrate, so povidone iodine (PI), a bone-dry powder, was chosen to be mixed with the 1:7 ferrate/resin powder. At 5 to 10% PI and 95% to 90% 1:7 powder, there was no change in TTH or strength of seal versus 100% 1:7 powder. Results showed that, with addition of as little as 2% PI, >log 4 kill of *Aspergillus niger* was achieved. The addition of PI to mixtures of ferrate/resin mixtures enable the hemostatic powder to have broad spectrum antimicrobial activity.

EXAMPLE 1

A level study of Povidone Iodine (PI) in 1:7 powder was tested with *Aspergillus niger* in a 7-day, daily re-challenge standardized test. A >4 log kill was achieved when the PI≥2%. Adding small amounts of PI to 1:7 powder had no effect on hemostasis but did provide the kill necessary to claim that the device created a 7-day antimicrobial barrier. This is a commercial breakthrough in that hospitals want and are now provided, an all-in-one product wherein hemostasis is achieved, exudate is absorbed, 24-48 hour dressing changes are eliminated and there is a reduction in hospital-acquired infections.

Dynamic Pneumatic Hemostasis Test Apparatus

Figure 8:
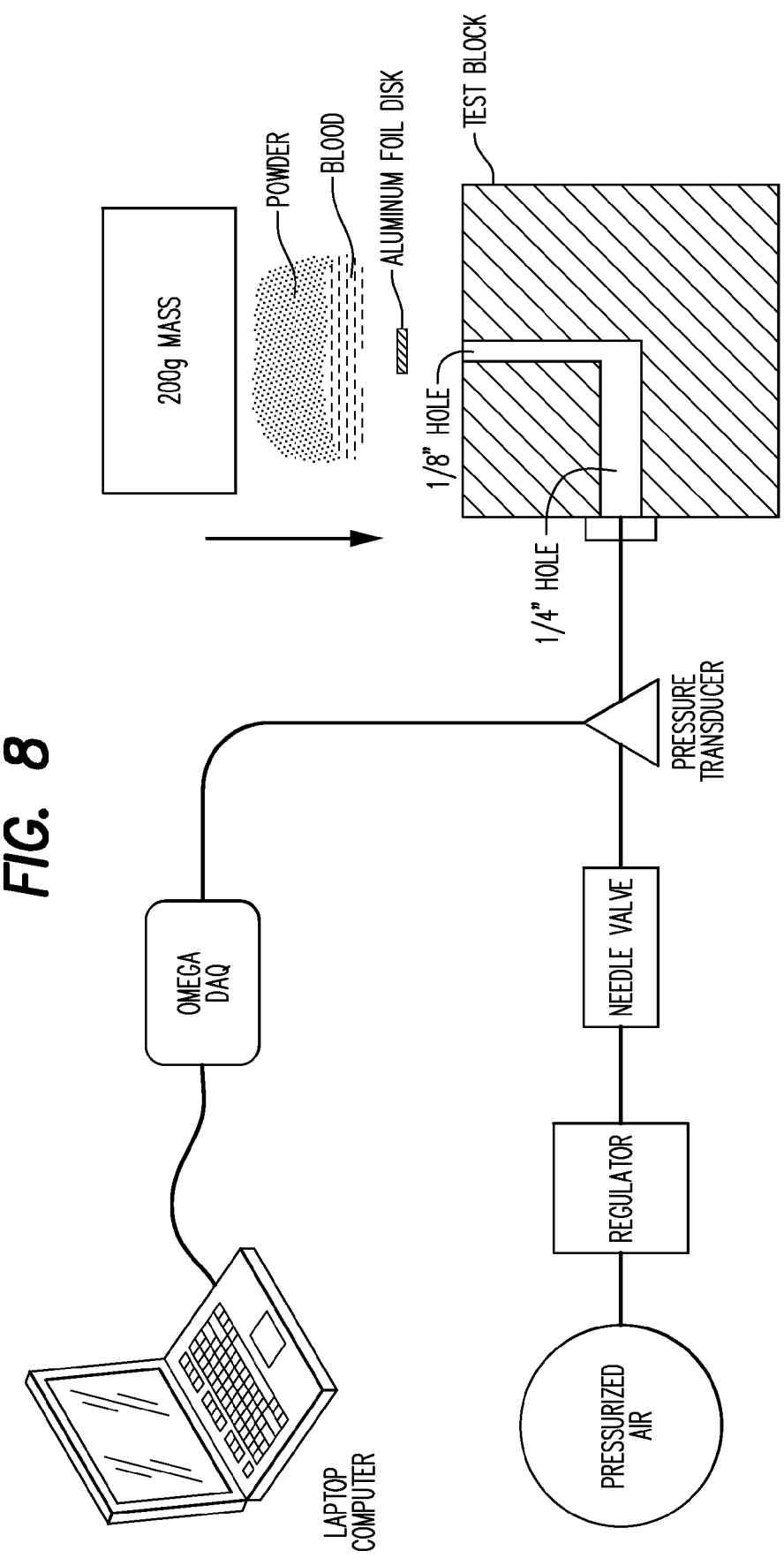
FIG. 8 is a simplified schematic view of an in vitro hemostasis testing system.

Referring to FIG. 8, the preferred apparatus for testing each test sample includes the use of air pressure to dislodge an aluminum disk adhered to a test block. Blood and powder are used to create the adhesive. The test measures the cohesive strength of the seal around the edges of the aluminum disk. A needle valve and an air regulator are used to control the pressure and rate of pressure increase into the test block. As the air pressure is increased, the disk will become dislodged and the air pressure will quickly drop. The maximum pressure is recorded. A traceable Fisher Scientific Manometer (8215 model number) is used to calibrate the data acquisition equipment (Omega OMB-DAQ-54).

Testing Procedure

The preferred procedure for testing each test sample for blood pressure to failure, i.e., when the test sample fails to maintain blood pressure under pressure within the test block, includes the following steps:
1) Connect the test block to the air pressuring system via the ¼" hole. Test block—An acrylic (or the like) test block. The block has a ¼" inlet hole for air pressure, and a ⅛" opening for testing.
2) Over the ⅛" opening a ¼" aluminum foil disk is placed to prevent power from filling the hole.
3) Over the foil disk place approximately 0.5 ml of blood.
4) Over the blood pour 1 g of test powder.
5) Over the test powder place a 200 g weight. And wait for 60 secs.
6) Now remove or leave the 200 gram weight as desired for the test.
7) Pressurize the system
8) Record the maximum pressure

EXAMPLE 2

Mixtures of Magnetite (Mag), a ferrate powder commercially available as QR Powder (QR) from assignee herein, Povidone Powder (PI), dry Hydrogen Resin and Hematite were tested in the above-described dynamic pneumatic hemostasis apparatus to compare the cohesive nature of each of the mixtures. Air pressure through a ⅛" hole was used to lift a small thin aluminum disk from a testing block. Over the aluminum disk was ~0.5 ml of whole EDTA treated bovine blood, and ~1 g of one of the powder mixtures. In one set of tests, a 200 gm weight was left in place over the powder, and in the other test set, the weight was removed before the system was pressurized. The system was capable of creating +500 mm Hg of pressure thru the ⅛" hole. The measurement of cohesion for each mixture was taken at the point when the air pressure caused the disk to lift and release the pressure held beneath. The results are summarized in Table 1.

TABLE 1

Cohesive Strengths (mm Hg) of Mixtures of Materials

| | Average mm Hg | Std dev |
|---|---|---|
| Tape Over Hole (Blank) | | |
| | 553.4 | |
| 200 g Mass Over Material | | |
| +44 micron Mag | 36.1 | 29.4 |
| 10 micron Mag | 40.1 | 18.3 |
| QR | 142.8 | 26.0 |
| 50/50 Mag-QR | 176.4 | 37.2 |
| 50/50 PI-QR | 193.0 | 43.7 |
| No Mass Over Material | | |
| Hematite | 28.8 | 7.9 |
| 10 micro Mag | 36.6 | 3.3 |
| 44 micron Mag plus | 37.1 | 6.5 |
| resin | 23.1 | 0.0 |
| 500µ ground resin | 31.6 | 2.6 |
| 10/90 Hematite-QR | 37.0 | 1.7 |
| 10/90 Mag-QR | 94.7 | 11.9 |
| 50/50 Mag-QR | 83.9 | 4.1 |
| QR | 60.7 | 17.4 |

TABLE 1-continued

Cohesive Strengths (mm Hg) of Mixtures of Materials

|  | Average mm Hg | Std dev |
|---|---|---|
| 5/5/90 PI-Mag-QR | 87.0 | 16.4 |
| 5/5/90 PI-Mag-Resin | 47.2 | 24.4 |
| 10/90 Mag-Resin | 51.4 | 21.1 |
| 10/90 PI- Res | 52.6 | 14.1 |
| 50/50 PI-QR | 58.6 | 25.1 |
| 25/25/50 PI-Mag-QR | 59.0 | 3.8 |
| 10/90 PI-QR | 59.2 | 2.3 |

Magnetite did not decrease the strength of the cohesive nature of the seal, while Hematite did. Magnetite and Hematite are both iron oxides, so it was a surprise to get better results with Magnetite than with Hematite.

EXAMPLE 3

In another series of experiments, the level of Magnetite added to QR, (a 1:7 mixture of ferrate/hydrogen resin) was varied from 0% to 100% and the weight in grams of mixture lifted by a standard magnet measured. As demonstrated, more Magnetite results in more total mass being held by the magnet. The strength of the magnet affects the amount of powder that can be held. There is a minimum amount of Magnetite needed for each device depending on the type of magnet used and the amount of powder needed to be applied.
QR powder was mixed with varying amounts of Magnetite and different types of magnets were used to determine the mass of powder that could be held.

TABLE 2

Mass Pick Up (gms) by Addition of Magnetite

| % QR | % Mag | Frig-Mag | Bk Cer | Cl—F-Su | F-Su | Sm Neo | Lg Neo |
|---|---|---|---|---|---|---|---|
| 100 | 0 | 0.0073 | 0.0021 |  | 0.0023 | 0.0017 | 0.0031 |
| 98.5 | 1.5 |  | 0.3718 |  | 0.2699 | 0.3038 | 0.3398 |
| 97 | 3 |  | 0.4995 |  | 0.398 | 0.5128 | 0.7616 |
| 90 | 10 | 0.1758 | 1.3976 | 0.0649 | 0.7071 | 1.459 | 2.4209 |
| 70 | 30 |  | 2.7205 |  |  | 2.0418 | 3.3509 |
| 30 | 70 | 0.4358 | 3.5408 | 0.3683 | 1.4665 | 2.5924 | 5.0837 |
| 0 | 100 |  |  |  |  |  | 10.1903 |

Three of the sets of data from Table 2 produced the graph shown in FIG. 1. The 30% Magnetite data with the F-Su magnet was estimated to produce the graph.

All Magnets are round discs

|  | diam | thickness |  |
|---|---|---|---|
| Frig. Magnets | 24 | 1 | Normal flexible refrigerator type magnetic |
| Bk Cer | 22 | 5 | Black ceramic magnet |
| CL-F-Su | 24 | 1 | Clean flexible neodymium magnetic (Edyne's SF-60) |
| F-Su | 24 | 0.5 | Flexible neodymium magnetic (Edyne's SF-35) |
| Sm-Neo | 13 | 1.5 | Silver hard neodymium magnet |
| Lg Neo | 24 | 1.5 | Silver hard neodymium magnet |

Magnetite is a 10 micron RV 99 grade sourced from Reiss Viking.
QR is sourced from Biolife, L.L.C., BP03-lot #927 and is a 1:7 mix of fusion ferrate and the hydrogen form of a 2% crosslinked sulfonated polystyrene ion exchange resin.

EXAMPLE 4

In another experiment, the distance from a small round neodymium magnetic to a 3% Magnetite/97% QR mixture was varied to give the results shown in FIG. 2. Because the magnet does not need to touch the powder, the Magnetite can be employed with many different types of applicators. The distance needed from the magnet to the power is determined by the amount of Magnetite in the product and the strength of the magnet, and the amount of powder desired.

EXAMPLE 5

A blood seal adhesion test was performed with mixtures of QR Powder with varying amount of Magnetite. A tenth (0.1) of a milliliter of stabilized bovine blood was spread out evenly on a one inch diameter circular template in a plastic tray. 300 mg of test powder was poured onto the template to cover the circular area. After three minutes of standing, the integrity of the seal (barrier) formed by the blood and test powder was evaluated by scraping with a small spatula. The amount of seal remaining after scraping was measured in an analytical balance. Qualitative readings of the following parameters were made: blood absorption, adhesion of the remaining seal, and % coverage of the seal after scrapping and is summarized in Table 3 below.

TABLE 3

Blood Seal Properties of QR with Magnetite

|  | (1) | (2) | (3) | (4) |
|---|---|---|---|---|
| % Magnetite | 100 | 70 | 50 | 30 |
| % QR | 0 | 30 | 50 | 70 |
| mg remaining seal | 0, 0, 0 | 16.4, 14.2, 14.0 | 13.6, 15.0, 16.2 | 16.2, 22.0, 21.6 |
| % cover | 0, 0, 0 | 25, 20, 20 | 30, 35, 25 | 30, 40, 40 |
| adhesion | none | very good | very good | very good |
| absorption | poor | good | good | good |

|  | (5) | (6) | (7) | (8) |
|---|---|---|---|---|
| % Magnetite | 10 | 3 | 1.5 | 0 |
| % QR | 90 | 97 | 98.5 | 100 |
| mg remaining seal | 19.0, 22.8, 25.3 | 23.0, 21.5, 22.8 | 17.5, 20.3, 20.5 | 19.7, 22.6, 20.1 |
| % cover | 35, 45, 50 | 50, 55, 50 | 40, 50, 50 | 40, 50, 55 |
| adhesion | very good | very good | very good | very good |
| absorption | good | good | good | good |

Magnetite is a 10 micron RV 99 grade sourced from Reiss Viking.
QR is sourced from BP03-lot #927 and is a 1:7 mix of fusion ferrate and the hydrogen form of a 2% crosslinked sulfonated polystyrene ion exchange resin.
The optimum range for hemostatic properties of mixtures of Magnetite and QR is from the 50% mix of Magnetite and QR to 100% QR. The optimum range was selected to provide a minimum of 30% coverage and 14 mg of seal remaining.

EXAMPLE 6

A blood seal adhesion test was performed with hydrogen resin with varying amounts of Magnetite. A tenth of a milliliter (0.1 ml) of stabilized bovine blood was spread out evenly on a one inch diameter circular template in a plastic tray. 300 mg of test powder was poured onto the template to cover the circular area. After three minutes of standing, the integrity of the seal (barrier) formed by the blood and test powder was evaluated by scraping with a small spatula. The amount of seal remaining after scraping was measured in an analytical balance. Qualitative readings of the following parameters were made: blood absorption, adhesion of the remaining seal, and % coverage of the seal after scrapping. The measures are recorded as a mean average of 3 to 6 runs.

TABLE 4

Blood Seal Properties of Mixtures of Hydrogen Resin and Magnetite

|  | (1) | (2) | (3) | (4) |
|---|---|---|---|---|
| % Magnetite | 100 | 70 | 50 | 30 |
| % H+Resin | 0 | 30 | 50 | 70 |
| mg remaining seal | 0 (wet paste) | 26.5 | 20.5 | 22.2 |
| % cover | 0 | 22 | 28 | 37 |
| adhesion | none | very good | very good | very good |
| absorption | poor | poor to fair | fair | good |

|  | (5) | (6) | (7) | (8) |
|---|---|---|---|---|
| % Magnetite | 20 | 10 | 3 | 0 |
| % H+Resin | 80 | 90 | 97 | 100 |
| mg remaining seal | 32 | 29.4 | 28.6 | 16.4 |
| % cover | 58 | 53.3 | 55 | 31 |
| adhesion | very good to exc | very good to exc | very good to exc | very good |
| absorption | good | good | good | good |

QR Control without Magnetite:
26.3 mg seal remaining; 50% coverage; very good to excellent adhesion; good blood absorption.
Magnetite is a 10 micron RV 99 grade sourced from Reiss Viking.
H+ Resin is a dried hydrogen form of 2% crosslinked sulfonated polystyrene ion exchange resin.
QR is from lot #390907 (exp April 2012) and is a 1:7 mix of fusion ferrate and H+ Resin.

The composition based on 100% Magnetite gave extremely poor blood seal properties. Blood seal properties picked up with the inclusion of 30-50% H+ Resin but blood absorption was poor to fair only and % coverage was below 30%. At higher H+ Resin levels of >70%, and in particular 80%, 90% and 97%, properties were equal to the QR control, a very effective commercial hemostatic powder. Without Magnetite, 100% H+ Resin gave less mg seal remaining and less coverage compared to the QR control. As will be shown herebelow, this composition does not have magnetic properties compared to a composition with Magnetite.

EXAMPLE 7

In another experiment, the ratio of ferrate-to-resin was changed to 1:12 and then 10% Magnetite added. Thompson discloses that the 1:7 ratio can sting an open wound such as a skin tear. Increasing the resin to 1:12 reduces the sting, but also reduces the strength of the seal. Adding the Magnetite to 1:12 strengthens the seal to about the same as 1:7 powder, thus reducing sting with no change in seal strength.

EXAMPLE 8

The addition of Magnetite also allows the material to be moved or held in place by the use of a magnet. The magnet, Magnetite, and dry ferrate/resin mixture (QR Powder) may be employed in combination with a pad, stick or other applicator with openings large enough to trap the powder, resulting in more "holding" power than either alone. For example a magnet behind a very open cell foam, a gauze bandage, or a flocked surface would hold powder more strongly than would either the magnet or foam, bandage or flocked surface alone. This was tested using a flocked substrate and a flat magnet.

Preferred Use Procedure

Figure 4:
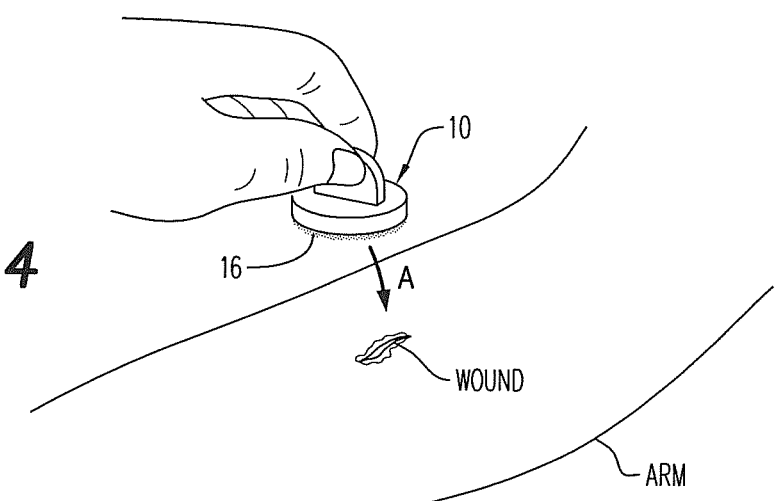
FIGS. 4 to 6 depict the sequence of deploying the Magnetite/hemostatic powder onto an open bleeding wound after being attached to the magnet shown in FIG. 3.
Figure 5:
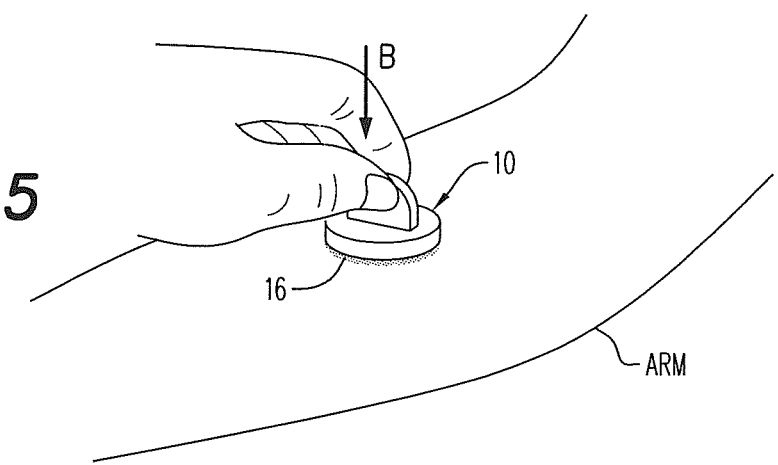
Figure 6:
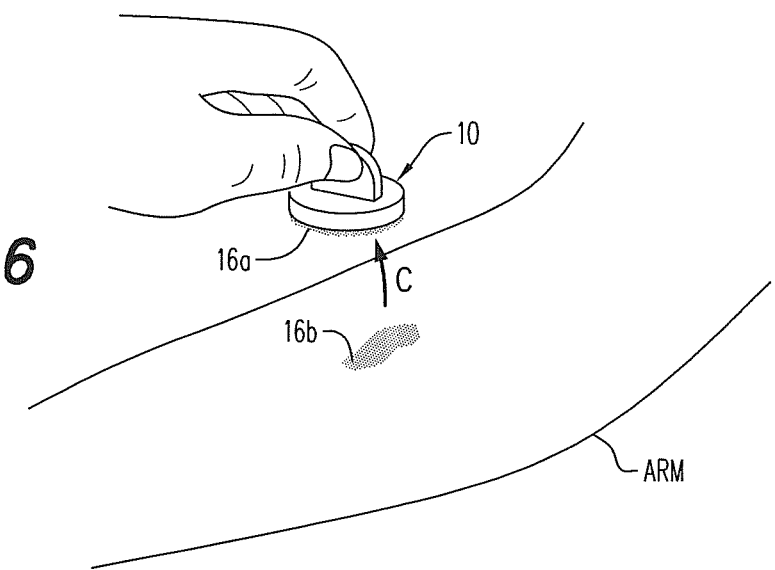

Referring now to FIGS. 3 to 6, a magnet device 10 having a round disc-shaped magnetic member 12 is used to lift a quantity of the Magnetite/hemostatic powder 14. After the magnet 10 has been positioned atop the Magnetite/powder pile 14 and a portion 16 thereof is attracted to the exposed surface of the magnet member 12, the magnet device 10 is lifted away and, as seen in FIGS. 4 to 6, is used to manually position the quantity of Magnetite/powder 16 over a bleeding wound in the direction of arrow A. Slight downward pressure in the direction of arrow B is applied to the magnet device 10 as seen in FIG. 5 and held in that position for a time sufficient for the ferrate hemostat to arrest blood flow. A scab at 16b in FIG. 6 is formed over the wound after which the magnetic device 10 is removed in the direction of arrow C. The remaining portion 16a of the Magnetite/powder remains attracted to the magnetic member 12 as it is lifted from the wound.

Figure 7:
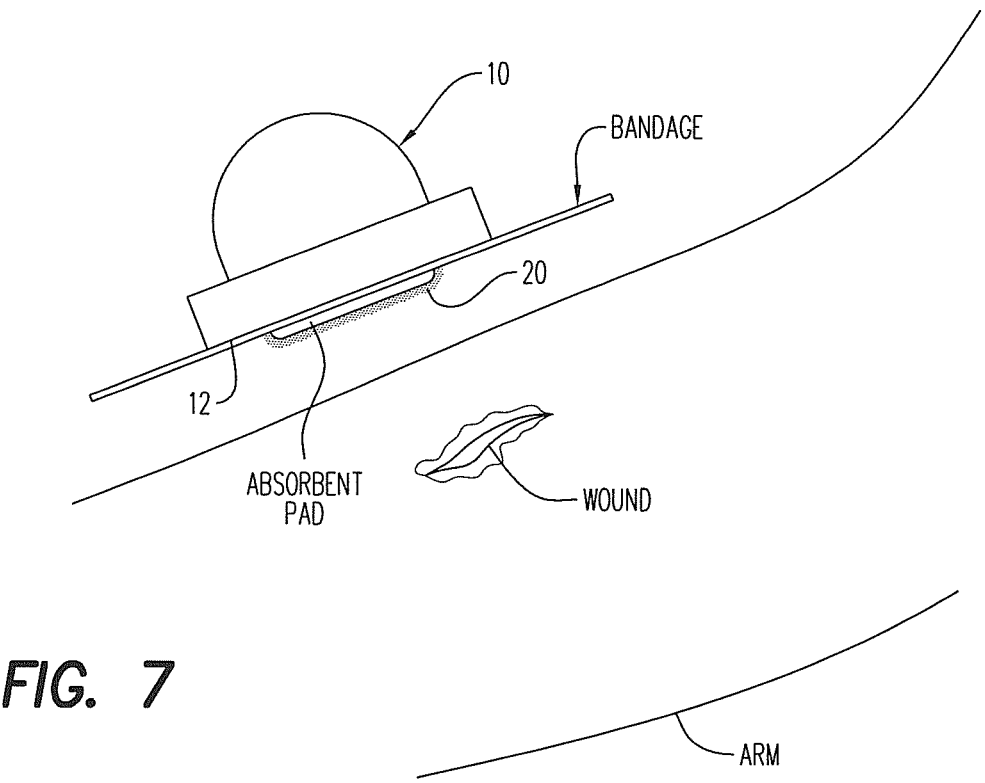
FIG. 7 is an alternate view of FIG. 4 wherein the Magnetite/hemostatic powder is attached to one surface of a bandage, the magnet being positioned against the opposite surface of the bandage.

In FIG. 7, the additional benefit of attracting Magnetite/hemostatic powder 20 against an absorbent pad of a bandage is there shown. The magnetic member 12 is positioned against the exposed surface of the bandage, after which the arrangement is positioned over the pile of Magnetite/hemostatic powder as shown in FIG. 3. A quantity of the powder 20 will be attracted and held against the absorbent pad of the bandage after which it may be applied under slight pressure against the wound as above described.

The application of Magnetite to influence delivery of medical devices including powders has been demonstrated for mixtures with ferrate and resin as well as with resin alone. It is within the scope of this invention to include the use of Magnetite in improving the delivery and control of application of all medical powders to the wound site. It is also well within the scope of this invention to include all other magnetic powders or materials aside from Magnetite to improve the delivery and control of application of all medical powders to the wound site.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:
1. A hemostatic system for applying a hemostatic agent in powder form directly onto a bleeding wound to arrest blood flow from the wound and to form a scab over the wound comprising:
    said hemostatic agent including potassium ferrate combined with powderous ion exchange resin in the hydrogen form and particulate or powderous magnetite; said potassium ferrate promoting blood clotting at the wound, said ion exchange resin forming a protective cover over the wound;
    said potassium ferrate, said resin, and said magnetite being present in a ratio of 1:7:0.4 to 1:7:8, respectively, of the weight of said hemostatic agent;

a magnet for magnetically attracting and holding a quantity of said composition against a surface of said magnet and for positioning said quantity of said composition against the wound;

a portion of said quantity of said composition forming the scab over the wound, a remainder of said quantity of said composition being magnetically held against said magnet to avoid spillage.

2. A hemostatic system for applying an anhydrous hemostatic agent in powder form directly onto a bleeding wound to arrest blood flow from the wound and to form a scab over the wound comprising:

said hemostatic agent including potassium ferrate combined with powderous ion exchange resin in the hydrogen form and particulate or powderous magnetite; said potassium ferrate promoting blood clotting at the wound, said ion exchange resin forming a protective cover over the wound;

said potassium ferrate, said resin and said magnetite being present in a ratio of 1:12:0.65 to 1:12:13, respectively, of the weight of said hemostatic agent;

a magnet for magnetically attracting and holding a quantity of said composition against a surface of said magnet and for positioning said quantity of said composition against the wound;

a portion of said quantity of said composition forming the scab over the wound, a remainder of said quantity of said composition being magnetically held against said magnet to avoid spillage.

3. A kit for arresting the flow of blood from a bleeding wound comprising:

a powderous hemostatic mixture of a salt ferrate and an ion exchange resin in the hydrogen form which will hydrate in the presence of blood thereby promoting clotting of the blood, said mixture also including a powderous Magnetite to form a homogenous powderous magnetic mixture;

a magnet for attracting and holding thereto a quantity of said magnetic mixture and for applying said magnetic mixture against the wound to effect hemostasis of, and scab formation over, the wound.

4. A hemostatic system comprising:

a composition including loose hemostatic powder capable of arresting blood flow from a bleeding wound and forming a scab over the wound;

said hemostatic powder including a salt ferrate and an ion exchange resin;

said composition also including powderous magnetite mixed uniformly with said hemostatic powder;

a magnet for magnetically attracting and holding a quantity of said composition against a surface of said magnet for positioning said quantity of said composition against the wound;

said magnetite being distributed throughout said composition allowing a much greater amount of said composition to be held by said magnet than the amount of magnetite in said composition;

a portion of said quantity of said composition forming the scab over the wound, a remainder of said quantity of said composition being magnetically held against said magnet to avoid spillage thereof.

\* \* \* \* \*